US010159784B2

United States Patent
Teutsch et al.

(10) Patent No.: US 10,159,784 B2
(45) Date of Patent: Dec. 25, 2018

(54) INITIALIZATION OF A DOSING UNIT FOR DRUG INFUSION

(71) Applicant: Roche Diabetes Care, Inc., Indianapolis, IN (US)

(72) Inventors: David Teutsch, Schupfen (CH); Peter Kettenmann, Waghaeusel (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 110 days.

(21) Appl. No.: 15/126,628

(22) PCT Filed: Feb. 18, 2015

(86) PCT No.: PCT/EP2015/053405
§ 371 (c)(1),
(2) Date: Sep. 16, 2016

(87) PCT Pub. No.: WO2015/139905
PCT Pub. Date: Sep. 24, 2015

(65) Prior Publication Data
US 2017/0106140 A1 Apr. 20, 2017

(30) Foreign Application Priority Data
Mar. 17, 2014 (EP) .................................... 14160177

(51) Int. Cl.
*A61M 5/14* (2006.01)
*A61M 5/142* (2006.01)
*A61M 5/36* (2006.01)

(52) U.S. Cl.
CPC .... *A61M 5/14244* (2013.01); *A61M 5/14216* (2013.01); *A61M 5/36* (2013.01);
(Continued)

(58) Field of Classification Search
CPC ............ A61M 5/36; A61M 2005/1402; A61M 2205/3331; A61M 2205/702; A61M 5/365
See application file for complete search history.

(56) References Cited

U.S. PATENT DOCUMENTS

| 5,813,842 A | * | 9/1998 | Tamari | ................ A61M 1/3621 |
| | | | | 417/477.1 |
| 6,190,354 B1 | * | 2/2001 | Sell | ................... A61M 25/1018 |
| | | | | 604/532 |

(Continued)

FOREIGN PATENT DOCUMENTS

| EP | 1319417 A1 * | 6/2003 | .......... A61M 1/3639 |
| EP | 1970677 A1 | 9/2008 | |

(Continued)

OTHER PUBLICATIONS

European Patent Office Written Opinion and Search Report dated May 7, 2015 in reference to co-pending European Patent Application No. PCT/EP2015/053405.

*Primary Examiner* — Scott Medway
(74) *Attorney, Agent, or Firm* — Dinsmore & Shohl LLP (57) ABSTRACT

Disclosed is a method for initializing a dosing unit (20) of an ambulatory infusion system, the method including carrying out a first priming routine. The first priming routine includes: providing the dosing unit (20) with a dosing chamber (202) having a minimal dosing chamber volume, a draining valve (205) being closed and a filling valve (204) being open. The first priming routine further includes measuring an initial reservoir fluid pressure $p_2$ and computing, a first priming volume $v_1$. The method further includes increasing the dosing chamber volume by the first priming volume $v_1$, with the first priming volume $v_1$ being computed such that a reservoir coupling conduit is filled with liquid drug substantially completely at the end of the dosing chamber volume increasing. The first priming routine fur- (Continued)

ther includes closing the filling valve (204) and opening the draining valve (205) and emptying the dosing unit (20) by decreasing the dosing chamber volume to the minimal dosing chamber volume. Disclosed are further a control unit for controlling operation of a dosing unit as well as an ambulatory infusion device.

15 Claims, 7 Drawing Sheets

(52) U.S. Cl.
CPC ............... *A61M 2005/1402* (2013.01); *A61M 2205/103* (2013.01); *A61M 2205/3331* (2013.01); *A61M 2205/702* (2013.01)

(56) References Cited

U.S. PATENT DOCUMENTS

| | | | | |
|---|---|---|---|---|
| 9,861,732 | B2 * | 1/2018 | Scarpaci | A61M 1/28 |
| 2003/0121517 | A1 * | 7/2003 | McFarland, Jr. | A61M 11/02 128/200.14 |
| 2008/0237142 | A1 * | 10/2008 | Carpenter | G01N 1/14 210/741 |
| 2009/0076433 | A1 * | 3/2009 | Folden | A61M 1/3643 604/4.01 |
| 2010/0034705 | A1 * | 2/2010 | Mundt | A61M 5/14216 422/400 |
| 2010/0192686 | A1 * | 8/2010 | Kamen | A61M 1/16 73/290 R |
| 2010/0305508 | A1 | 12/2010 | Franks | |
| 2011/0257593 | A1 * | 10/2011 | Kalpin | A61M 5/14276 604/111 |
| 2013/0239666 | A1 * | 9/2013 | Carpenter | B01D 61/147 73/61.72 |
| 2015/0314058 | A1 * | 11/2015 | O'Mahony | A61M 1/3639 417/63 |
| 2017/0326282 | A1 * | 11/2017 | Wilt | A61M 1/1086 |
| 2018/0071450 | A1 * | 3/2018 | Ruhland | G06F 19/00 |

FOREIGN PATENT DOCUMENTS

| | | | | |
|---|---|---|---|---|
| EP | | 2163273 A1 | 3/2010 | |
| EP | | 2881128 A1 | 6/2015 | |
| WO | WO | 8705225 A2 * | 9/1987 | ........ A61M 5/16809 |
| WO | | 2012126745 A2 | 9/2012 | |

* cited by examiner

INITIALIZATION OF A DOSING UNIT FOR DRUG INFUSION

FIELD OF DISCLOSURE

The present invention relates to a method for initializing a dosing unit of an ambulatory infusion system, to a control unit for controlling operation of a dosing unit of an ambulatory infusion system, and to an ambulatory infusion device.

BACKGROUND

Prior Art

Ambulatory infusion devices are well known in the art for example in the therapy of Diabetes Mellitus by Continuous Subcutaneous Insulin Infusion (CSII) as well as in pain therapy or cancer therapy and are available from a number of suppliers, such as Roche Diagnostics GmbH, Germany, or Medtronic MiniMed Inc., CA, USA.

According to a classic and well-established design, those ambulatory infusion devices are typically of the syringe-driver type. A number of drawbacks of such devices are known in the art. In particular, they have a limited precision because they involve delivering very small drug amounts, typically in the Nanoliter range, out of a drug cartridge having an overall drug volume in the millilitre range. Therefore, additional concepts and architectures have been proposed which use a dedicated dosing unit downstream from the drug reservoir. Such a dosing unit comprises a miniaturized pump, e.g., a micro membrane pump or a micro piston pump. It is adapted to couple to a liquid drug reservoir and is further especially designed for precise dosing of small volumes in the small Microliter range or Nanoliter range. While several designs for such dosing units are known in the art, they are rather complex, most of them are expensive and/or critical with respect to large scale.

The EP1970677A1 discloses a system with a miniaturized piston pump as dosing unit. This dosing unit includes a dosing cylinder that is repeatedly coupled to and filled from a larger reservoir, followed by coupling the dosing cylinder to an infusion line and infusing the liquid drug out of the dosing cylinder in incremental steps and over an extended time period. For alternatively coupling the dosing cylinder to the reservoir and the infusion line, a valve system is proposed.

Figure 1:
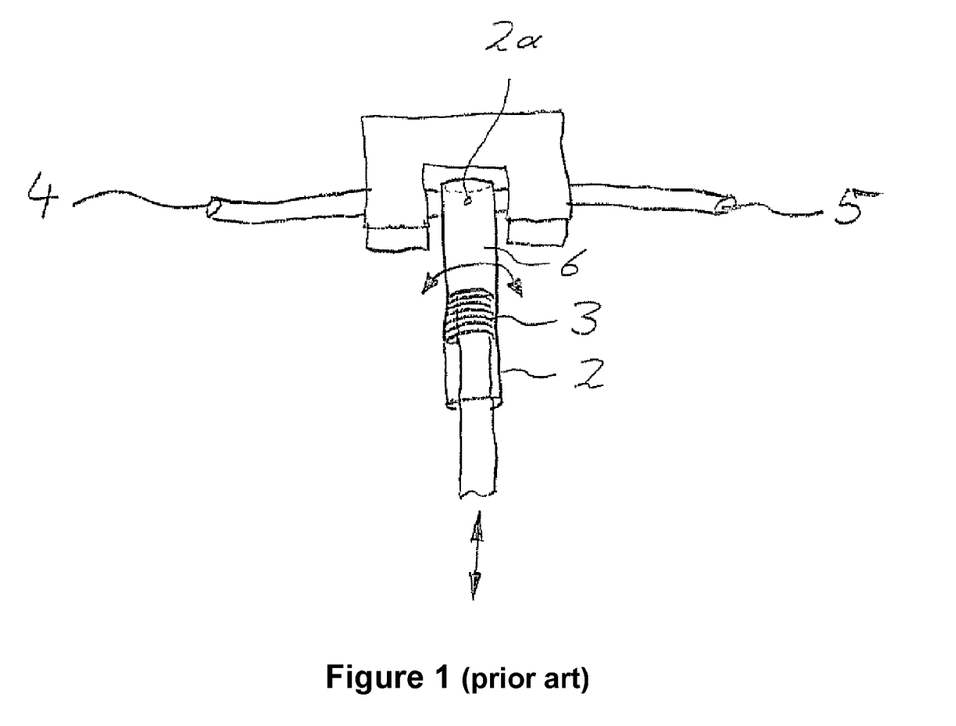
FIG. 1 (discussed above) schematically shows an exemplary dosing unit which may be used in the context of the present disclosure.

For illustrative purposes, reference is made to FIG. 1, showing an exemplary dosing unit according to the disclosure of EP1970677A1 in a schematic structural view. The dosing unit includes a dosing cylinder (also referred to as "pump cylinder") 2 with a dosing chamber 6 that may be varied in steps or increments by displacing a dosing piston (also simply referred to as "piston") 3. The dosing cylinder 2 may have a single opening or aperture 2a for filling the variable dosing chamber with drug via a supply tube 4 or reservoir coupling conduit 4 from a drug container and expelling drug from the variable dosing volume into a catheter or infusion line 5. The aperture 2a that is arranged in a proximal wall section of the dosing cylinder 2 may—by rotating the dosing cylinder 2, about its longitudinal axis with respect to a sealing stationary member (not referenced, U-shaped piece in FIG. 1)—be alternatively a alternatively aligned with a reservoir coupling port or an outlet port, thereby alternatively coupling the dosing chamber 6 with the reservoir coupling conduit 4 or the infusion line 5. The pump cylinder and the stationary member, in combination, accordingly form a valve arrangement with a filling valve for coupling with the reservoir coupling conduit 4 and a draining valve for coupling with the catheter. Depending on the rotational position of the dosing cylinder either of the filling valve or the draining valve may be opened, with the other valve being closed. In an intermediate state, both the filling valve and the draining valve are closed. Simultaneous opening of the filling valve and the draining valve is prevented by the design of the valve arrangement. The process of filling the dosing chamber may also be referred to as "charging" and the process of expelling drug out of the dosing chamber as "discharging". The filling valve may accordingly be referred to as "charging valve" and the draining valve may be referred to as "discharging valve".

SUMMARY OF DISCLOSURE

A major critical aspect and issue of concern with respect to ambulatory infusion systems that include a dedicated dosing unit is the handling of gas, in particular air, in the fluid path. While it would be generally desirable to provide a drug reservoir completely filled with liquid drug, e.g. a liquid insulin formulation, and without any air, this is hardly achievable under the circumstances that are typically given for ambulatory infusion systems and with reasonable costs and handling effort. In addition, outgassing of air that is initially solved in the liquid drug is known to occur during application, e.g. due to temperature variations. Furthermore, the dosing unit is, in contrast to the classical syringe driver design, not integral with the drug reservoir but fluidically coupled with the drug reservoir via a fluidic reservoir coupling conduit that is also filled with air in the supply state. Air may further be drawn into the dosing chamber in case of a faulty or improperly coupled fluidic connection.

It is an object of this invention to provide an improved method for initializing a dosing unit of an ambulatory infusion system, and to a corresponding control unit as well as a corresponding ambulatory infusion device. In particular, it is an object of the present invention to provide a method and a control unit which allow reliable priming in the presence of gas in the fluidic system of the ambulatory infusion system.

Even though many drugs that are infused via an ambulatory infusion system, such as insulin, are infused into the subcutaneous tissue rather than a vein, the unintended infusion of air is associated with a corresponding lack or reduction of infused drug which may—under some circumstances—result in severe medical complications.

Here and in the following, the terms "initializing" and "initialization" are generally referred to preparatory handling steps that need to be carried out when using a new dosing unit in the ambulatory infusion system. The dosing unit is typically replaced every few days. The "priming" is part of the initialization procedure and refers to the initial filling of the fluidic conduits with liquid drug.

According to the present invention, these objects are achieved through the features of the independent claims. In addition, further advantageous embodiments follow from the dependent claim as well as from the general description and the description of exemplary embodiments.

According to one aspects, objects of the present invention are achieved by providing a method for initializing a dosing unit of an ambulatory infusion system. In the following description of the method, it is assumed that the individual steps are, where not mentioned otherwise, are carried out in accordance with the order of presentation. It is further assumed that no further actions and in particular no variation of the dosing chamber volume and/or valve switching is performed between the here-described steps, such that the final fluidic configuration resulting from each step at the same time defines the initial or starting configuration for the next following step.

The method includes carrying out a first priming routine. The first priming routine includes the step of providing the dosing unit with a dosing chamber of the dosing unit having a minimal dosing chamber volume, the draining valve being closed and the filling valve being open. This step may include actuating the filling valve and/or the draining valve of the dosing unit if the filling valve and/or the draining valve are not in those states. and opening a filling valve of the dosing unit. This step may further include determining the state of the filling valve and the draining valve respectively. This step may further include reducing the dosing chamber volume to a minimum dosing chamber volume if this is not initially the case.

The first priming routine further includes the step of measuring an initial reservoir fluid pressure $p_2$ and computing, based on the initial reservoir fluid pressure $p_2$, a first priming volume $v_1$, with the initial reservoir fluid pressure $p_2$ being a fluidic pressure inside a liquid drug reservoir. The liquid drug reservoir is fluidic coupled with the dosing chamber via a reservoir coupling conduit and the opened filling valve. The initial reservoir fluid pressure $p_2$ is favourably an equilibrium pressure with no or negligible liquid movement. The initial reservoir fluid pressure $p_2$ is measured as differential pressure to a reference pressure $p_{ref}$ which may especially be a surrounding environmental pressure.

The first priming routine further includes the step increasing the dosing chamber volume by the first priming volume $v_1$. The first priming volume $v_1$ is computed—in dependence of the initial reservoir fluid pressure $p_2$—such that the reservoir coupling conduit is filled with liquid drug substantially completely at the end of the dosing chamber volume increasing. The air/gas that is present inside the reservoir coupling conduit prior to this step is also suck into the metering chamber in this step. A mixture of liquid drug and gas is accordingly present in the metering chamber at the end of this step, with the total volume equalling the first priming volume $v_1$.

The first priming routine further includes the step closing the filling valve and opening the draining valve. The first priming routine further includes emptying the dosing unit by decreasing the dosing chamber volume to the minimal dosing chamber volume. Thereby, the mixture of liquid and air/gas is expelled via the draining valve. Here and in the following, it is assumed that the minimal dosing chamber volume is negligible or zero.

While carrying out the here-described first priming routines as well as optional further routines of the method, the dosing unit is not fluidic coupled to the patient such that no drug is infused. Instead, an outlet of the draining valve is, directly or via a already connected infusion line, fluidic coupled to the environment.

In the context of the present invention, the dosing chamber is a fluidic chamber that is, during regular operation, i.e., for the drug infusion, repeatedly filled with liquid drug by increasing the dosing chamber volume, followed by dosing drug out of the dosing chamber by decreasing the dosing chamber volume continuously or in substantially infinite incremental steps over an extended time period. The dosing chamber is coupled to a liquid drug reservoir via the filling valve that is actively controlled to alternatively be in an opened or closed state. The dosing chamber is further coupled to an infusion path via a draining valve that is also actively controlled to alternatively be in an opened or closed state. It is further assumed that, only the filling valve or the draining valve may be in the opened state at the same time, but not both of them. This may be achieved by corresponding control of the valves and/or by a corresponding mechanical valve design as will be discussed further below. Both of the filling valve and the draining valve may, however, be controlled to simultaneously be in the closed state. In some embodiment, the mechanical valve design is such that a temporary state where both the filling valve and the draining valve are closed is always passed by design when switching between open filling valve and open draining valve. A dosing unit that may be initialized using the disclosed method is, e.g., a dosing unit as schematically shown in FIG. 1. Further options and alternatives for the dosing unit design are discussed further below.

The initial reservoir fluid pressure $p_2$ is the equilibrium fluid pressure inside the drug reservoir which is typically realized as any of a flexible bag or pouch, a rigid cartridge with an e.g. spring-biased movable piston, or a semi-rigid reservoir with a rigid shell and a flexible cover shell, e.g. a foil. The initial reservoir fluid pressure may be measured by a pressure sensor. A suited arrangement of a pressure sensor in a dosing is discussed further below.

In some embodiments, the first priming routine includes computing the first priming volume $v_1$ as $$v_1 = V_0 \cdot \frac{p_{ref}}{p_{ref} + p_2} + V_S,$$

with $V_0$ being the design-given fluidic volume of the reservoir coupling conduit, $p_{ref}$ being a reference pressure, in particular an surrounding environmental pressure, and $V_s$ being a safety margin volume. The rationale for this embodiment is based on the assumption of a virtual isotherm where the product of volume and pressure are constant: At the reference pressure $p_{ref}$, i.e., for $p_2=0$, the term $$\frac{p_{ref}}{p_{ref} + p_2}$$

equals one. That is, the first priming volume equals in this case the sum of the fluidic volume $V_0$ of the reservoir coupling conduit plus the safety margin $V_s$, with the safety margin volume compensating for any air/gas that may be suck into the dosing chamber from the drug reservoir as well as mechanical tolerances and the like. For the case of a relative over pressure in the reservoir, i.e., for $p_2>0$, the above mentioned term is smaller than one, reflecting the fact that the air/gas that is initially present in the reservoir coupling conduit is compressed, in contrast to the liquid by which it is replaced. For any relative under pressure in the reservoir, i.e., for $p_2<0$, the same applies in an analogue way.

The reference pressure $P_{ref}$ may be an actual environmental air pressure or a nominal environmental air pressure, such as 1013 mbar.

In some embodiments, the method further includes, prior to carrying out the first priming routine, carrying out a sensor calibration routine. The sensor calibration routine includes the step of providing the dosing unit in an initial state with the dosing chamber being gas-filled and both of the filling valve and the draining valve being closed, resulting in the dosing chamber being fluidic isolated. This step may include closing both of the filling valve and the draining valve. This step may further include determining the state of the filling valve and the draining valve respectively.

The sensor calibration routine further includes the step of decreasing the dosing chamber volume, thereby compressing the gas inside the dosing unit to a compression factor $c_1$. The sensor calibration routine further includes reading, at the compression factor $c_1$, an output value $p_1^*$ of a pressure sensor in fluidic coupling with the dosing chamber and computing, based on the output value $p_1^*$ and the compression factor $c_1$, a pressure sensor calibration, and storing the computed calibration.

The sensor calibration routine further includes the step of opening the draining valve with the filling valve staying closed. The sensor calibration routine further includes further includes the step of emptying the dosing cylinder by further decreasing the dosing chamber volume to the minimum dosing chamber volume. Thereby the gas is expelled out of the dosing chamber via the draining valve.

The sensor calibration routine that may be carried out prior to carrying out the first priming routine calibrates a pressure sensor of the dosing unit that is employed, in the following before-described first priming routine, for measuring the fluidic reservoir pressure as relative pressure and may optionally be used in a further following second priming routine as described further below. The same pressure senor may further be used during subsequent infusion, especially for detecting a clogged/occluded system. The term "calibration" is to be understood in the sense of determining a typically but not necessary linear relationship between the measured pressure p and the corresponding output value, e.g. voltage value $p^*$.

The gas that is initially present in the dosing chamber at beginning of the pressure calibration routine may in principle be environmental air. However, since the dosing chamber is, during application, filled with liquid drug that is infused into a patient's body, it is favourably sterile air or an inert gas. Dosing units may be provided by a supplier readily filled with such gas in a sterile box or other packaging.

It is assumed that, at the initial state. the gas inside the dosing chamber is at known environmental pressure, i.e. reference pressure $P_{ref}$, which may be achieved by providing the dosing unit with the draining valve being opened. If this is not the case or can not be guaranteed, pressure sensor calibration routine may include, prior to the step of providing the dosing unit with both of the filling valve and the draining valve being closed, opening the draining valve for a time period sufficiently long for pressure equalization.

The compression factor that results from any decrease of the dosing chamber volume is proportional to the reciprocal relative volume change. For example, halving the dosing chamber to a compression factor of c=2 doubles the gas pressure inside the dosing chamber. For any dosing chamber volume, the compression factor and the gas pressure is accordingly known, thus enabling a pressure sensor calibration.

Further aspects and variants of a sensor calibration routine in accordance with the present disclosure are discussed further below in the context of exemplary embodiments.

In some embodiments, the method further includes, following carrying out the first priming routine, carrying out a second priming routine. The second priming routine includes closing the draining valve and opening the filling valve. The second priming routine further includes increasing the dosing chamber volume by a second priming volume $v_2$. Thereby, liquid drug is suck out of the liquid drug reservoir into the dosing unit. In embodiments including a second priming routine, a finalization routine may optionally be carried out following the second priming routine. The steps of such a finalization routine is described further below in the context of exemplary embodiments.

The second priming routine further includes closing the filling valve with the draining valve staying closed, resulting in the dosing chamber being fluidic isolated. The second priming routine further includes varying the dosing chamber volume and monitoring, during the variation, a dosing chamber pressure $p_C$, and stopping the variation upon the dosing chamber pressure $p_C$ equalling a reference pressure. The second priming routine further includes computing, based on an amount of variation of the dosing chamber volume, an air volume $V_{air}$ of air inside the dosing chamber.

In order to determine whether the dosing chamber volume needs to be increased or decreased, an initial dosing chamber pressure $p_{C,0}$ is measured after fluidic isolating the dosing chamber and the sign of the initial dosing chamber pressure $p_{C,0}$ relative to the reference pressure $p_{ref}$ is used as criterion for deciding on increasing or decreasing the dosing chamber volume. If the initial dosing chamber pressure $p_{C,0}$ is negative, thus indicating an initial underpressure/negative pressure, the dosing chamber volume is subsequently decreased for equalizing with the reference pressure $p_{ref}$. If the initial dosing chamber pressure $P_{C,0}$ is positive, thus indicating an initial overpressure/positive pressure, the dosing chamber volume is subsequently increased for equalizing with the reference pressure $P_{ref}$.

In some embodiments including a second priming routine, the second priming routine includes the comparing the air volume $V_{air}$ with a pre-set threshold air volume $V_{air,threshold}$ and providing an alert if the air volume $V_{air}$ exceeds the threshold air volume $V_{air,threshold}$. The threshold air volume $V_{air,threshold}$ may depend on a variety of general and/or patient specific factors, such as a patient's total daily drug volume, and is determined in accordance with an overall risk policy and/or based on regulatory requirements. Air in the dosing chamber may be sucked in from the liquid drug reservoir as described before, or may be sucked in from the environmental due to a leaking fluidic coupling or any other leakage of the fluidic path as hazardous situation.

In some embodiments including a second priming routine, the second priming routine includes taking into account a mechanical compliance of limiting walls of the dosing chamber for computing the air volume $V_{air}$. For this type of embodiment, the air volume $V_{air}$ may be computed according to the formula:

$$V_{air} = (\Delta V - \Delta V_{compliance}) \cdot \left(1 + \frac{p_{ref}}{p_{c,0}}\right),$$

with $\Delta V$ being the change volume by which the dosing chamber volume is varied for pressure equalization and $\Delta V_{compliance}$ being the design-given amount by which the dosing chamber volume varies due to wall compliance. This formula is based on the assumption of virtual isotherm, i.e. with the product of volume and pressure being constant. If the walls of the dosing chamber and are sufficiently stiff to allow ignoring mechanical compliance, $\Delta_{compliance}$ may be set to zero.

For embodiments where increasing or decreasing of the dosing chamber volume is achieved by displacing a dosing piston of the dosing unit in a dosing cylinder, and the dosing piston is displaceable in incremental steps, the before-given formula may be rewritten to $$V_{air} = (m - m_{compliance}) \cdot V_{step} \cdot \left(1 + \frac{P_{ref}}{p_{c,0}}\right),$$

with m being the number of steps by which the piston is displaced for pressure equalization, $m_{compliance}$ being the design-given number of steps for compensating mechanical wall compliance, and $V_{step}$ being the design-given incremental volume change per step. The number of steps m may be determined by counting, while varying the dosing chamber volume, the number of steps that is required pressure equalization.

In some embodiments, increasing of the dosing chamber volume is achieved by displacing a dosing piston of the dosing unit into a distal direction and decreasing of the dosing chamber volume is achieved by displacing the dosing piston into an opposite proximal direction. This is the case for dosing units that include a dosing cylinder with a bore-like axial recess and a dosing piston that is slidably and sealing received in the recess, as shown, e.g. in FIG. 1. For this type of embodiment, the piston accordingly forms a movable limiting wall of the dosing chamber, while other limiting walls of the dosing chamber are formed by the dosing cylinder. For this type of embodiment, the dosing unit is designed as syringe-like positive displacement pump, with the dosing cylinder corresponding to the syringe body.

In some embodiments, opening and closing of the filling valve and the draining valve includes rotating a common shutoff body of the dosing unit. Corresponding dosing unit designs are disclosed in the European patent application EP13195599.9. Alternatively, a common shutoff-body may be shifted, i.e. linearly displaced, or separate shutoff-bodies of the filling valve and draining valve may be rotated or shifted. In alternative embodiments, opening and closing of the filling valve and the draining valve is achieved by relative movement, e.g. rotation of a dosing cylinder of the dosing and a stationary member, as show in FIG. 1 and the EP1970677A1.

According to a further aspect, objects of the present invention are achieved by providing a control unit. The control unit is designed for controlling operation of a dosing unit of an ambulatory infusion system. The control unit includes a metering chamber volume controller, a valve controller, and a pressure sensor interface. The control unit is designed for controlling execution of a first priming routine. The first priming routine includes:
 providing the dosing unit with a dosing chamber of the dosing unit having a minimal dosing chamber volume, a draining valve of the dosing unit being closed and a filling valve of the dosing unit being open;
 measuring an initial reservoir fluid pressure $p_2$ and computing, based on the initial reservoir fluid pressure $p_2$, a first priming volume $v_1$, with the liquid drug reservoir being fluidic coupled with the dosing chamber via a reservoir coupling conduit and the opened filling valve;
 increasing the dosing chamber volume by the first priming volume $v_1$, with the first priming volume $v_1$ being computed such that the reservoir coupling conduit is filled with liquid drug substantially completely at the end of the dosing chamber volume increasing;
 closing the filling valve and opening the draining valve;
 emptying the dosing unit by decreasing the dosing chamber volume to the minimal dosing chamber volume.

The control unit is realized by electronic circuitry, based on programmable components such as one or more micro controllers or microcomputer, and associated peripheral circuitry, such as power supply circuitry, safety circuitry and actuator driver circuitry. The control flow may be hard-coded or, fully or partly, be realized by a computer program product including a non-transient computer readable medium having stored therein computer program code. The non-transient computer readable medium may especially be realized as Read-Only-Memory (ROM) or non-volatile Random Access Memory (RAM).

In some embodiments of the control unit, the control unit is further designed for controlling, prior to controlling execution of the first priming routine, execution of a sensor calibration routine by:
 controlling, via the valve controller, the valve actuator to close the filling valve and the draining valve, resulting in the dosing chamber being fluidic isolated;
 controlling, via the dosing chamber volume controller, the dosing chamber actuator to decrease the dosing chamber volume, thereby compressing the gas inside the dosing unit to a pre-set compression factor c;
 reading, via the pressure sensor interface, at the compression factor c an output value $p_1^*$ of the pressure sensor, computing, based on the output value $p_1^*$ and the compression factor c, a pressure sensor calibration, and storing the computed calibration;
 controlling, via the valve controller, the valve actuator to open the draining valve with the filling valve staying closed;
 controlling, via the dosing chamber volume controller, the dosing chamber actuator to further decrease the dosing chamber volume, thereby expelling the gas out of the dosing chamber.

In some embodiments of the control unit, the control unit is further designed for controlling, following to controlling execution of the first priming routine, controlling execution of a second priming routine. The second priming routine includes:
 closing the draining valve and to open the filling valve;
 increasing the dosing chamber volume by a second priming volume $v_2$;
 closing the filling valve with the draining valve staying closed, resulting in the dosing chamber to be fluidic isolated;
 varying the dosing chamber volume and monitoring, during the variation, a chamber pressure $p_C$ inside the dosing chamber, and stopping the variation upon the chamber pressure $p_C$ equalling a reference pressure $P_{ref}$;
 computing, based on an amount of variation of the dosing chamber volume, an air volume $v_{air}$ of air inside the dosing chamber.

In some embodiments of the control unit, the dosing chamber volume controller is configured for controlling the dosing chamber actuator to alternatively increase or decrease the dosing chamber volume continuously or in incremental steps.

In some embodiments of the control unit, the valve controller is designed for controlling a rotary valve motor as valve actuator and the dosing chamber volume controller is designed for controlling a rotary dosing chamber motor as dosing chamber actuator.

The control unit may further be designed for controlling the execution of a method for initializing a dosing unit in accordance according to any embodiment for such a method as generally described before as well as further below in the context of exemplary embodiments. Therefore, any disclosed embodiment of such a method likewise discloses a corresponding embodiment of a control unit that is designed for controlling execution of the disclosed method.

According to a still further aspects, objects of the present invention are achieved by providing an ambulatory infusion device. The ambulatory infusion device includes a control unit according as generally described before and further below in the context of exemplary embodiments. The ambulatory infusion device further includes a valve actuator, the valve actuator being operatively coupled to the valve controller and being designed for engaging a valve actuator coupler of a dosing unit. The ambulatory infusion device further includes a dosing chamber actuator, the dosing chamber actuator being operatively coupled to the dosing chamber actuator controller and being designed for engaging a movable limiting wall of the dosing chamber. The ambulatory infusion device further includes a casing, the casing enclosing the control unit, the valve actuator and the dosing chamber actuator. The ambulatory infusion device further includes a dosing unit interface, the dosing unit interface being designed for releasably coupling the ambulatory infusion device with the dosing unit such that the valve actuator releasably engages a valve actuator coupler of a dosing unit.

DETAILED DESCRIPTION OF EXEMPLARY EMBODIMENTS

In the following, exemplary embodiments in accordance with the present invention are described in more detail with additional reference to the figures.

FIG. 1 shows a dosing unit which is—as such—known from the prior art as exemplary embodiment of a dosing unit that may be used in the context of the present disclosure. Reference is made to the corresponding section of the Summary of Disclosure for a more detailed description and discussion of such a dosing unit.

Figure 2:
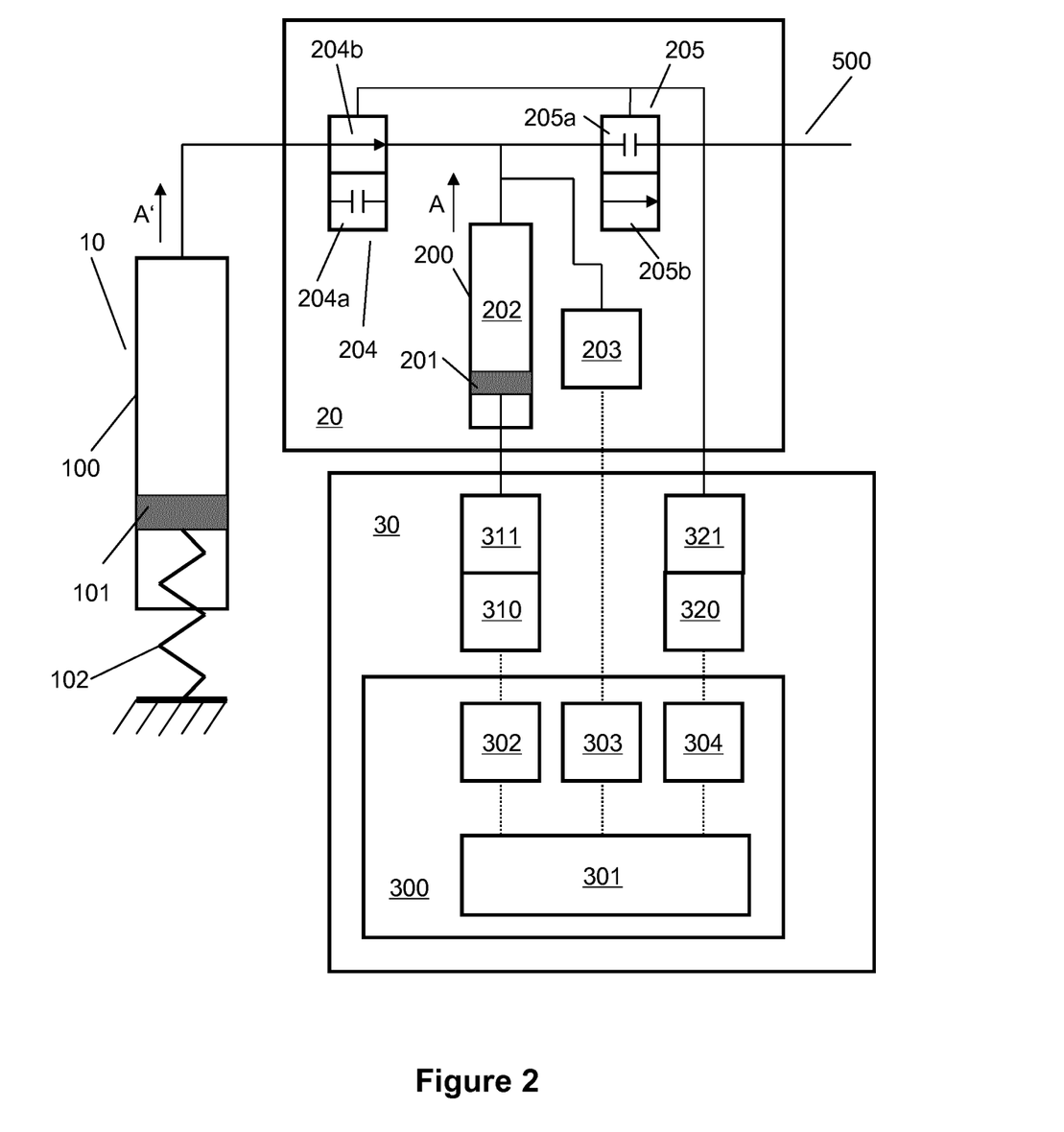
FIG. 2: shows an ambulatory infusion system that includes an exemplary ambulatory infusion device in accordance with the present disclosure, in a schematically view.

FIG. 2 shows an exemplary ambulatory infusion system together with associated components in a schematic structural view together with associated components. The exemplary ambulatory infusion system includes a drug reservoir unit 10, a dosing unit 20 and an ambulatory infusion device 30.

The drug reservoir 10 is exemplarily shown as cylindrical cartridge body 100 which receives a displaceable piston 101 in a sealing and sliding way. The piston 101 is biased by an optional biasing spring 102 in the direction A'. Alternatively, the liquid drug reservoir 100 may be realized in a different way, e.g. as flexible bag or pouch or as semi-flexible drug reservoir with a rigid body and a flexible cover which allows the liquid-filled volume to vary.

The dosing unit 20 includes a dosing cylinder 200 with a bore-like recess which receives a displaceable dosing piston 201 in a sealing and sliding way, thus forming a syringe-like arrangement with a dosing chamber 202 of variable volume. The volume of the dosing chamber 202 may be increased by displacing the dosing piston 201 in a distal direction and may be decreased by displacing the dosing piston 201 in a proximal direction A. The dosing cylinder 200 and the piston 201 accordingly form, in combination, a miniaturized dosing piston pump. Via a common fluidic port (not referenced) at the proximal end of the dosing cylinder 200, the dosing cylinder 200 and in particular the dosing chamber 202 is fluidic coupled with a filling valve 204a, 204b, and a draining valve 205a, 205b. Each of the filling valve may alternatively be in a closed state 204a, 205a, or an open state, 20a, 205b, respectively. The filling valve is further fluidic coupled to the liquid drug reservoir 10. The draining valve is further fluidic coupled to an infusion line 500.

The dosing unit 20 further includes a pressure sensor 203 that is realized as relative pressure sensor for pressure measurement relative to an environmental reference pressure. The pressure sensor may be realized in a number of ways, e.g. as piezo-resistive or capacitive sensor or as optical pressure sensor. The pressure sensor 203 is fluidic coupled to the fluidic port of the dosing cylinder 200. If the filling valve is open, 204b, and the draining valve is closed, 205a, a fluidic coupling is present between the liquid drug reservoir 10 and the pressure sensor 203 and the dosing chamber 202, such that the pressure that is measured by the pressure sensor 203 corresponds, in a static or equilibrium state, to the reservoir pressure. If the draining valve is open, 205b, and the filling valve is closed, 204a, a fluidic coupling is present between the infusion line 50 and the pressure sensor 203 as well as the dosing chamber 202, such that the pressure that is measured by the pressure sensor 203 corresponds, in a static or equilibrium state, to infusion line pressure. both of filling valve and the draining valve are closed, the dosing chamber 202 and the pressure sensor 203 are fluidic isolated from both of the drug reservoir 10 and the infusion line 50.

The ambulatory infusion device 30 includes a control unit 300, a dosing chamber drive 310, 311, and a valve drive 320, 321.

The dosing chamber drive 310, 311 includes a dosing chamber actuator 310 that is exemplarily considered as a rotary dosing chamber motor 310, e.g. a stepper motor, a standard DC motor, or a brushless DC motor. In an operable state, output element, e.g. a rotary output shaft, of the dosing chamber motor 310 is coupled to the dosing piston 201. Between the motor output shaft and the dosing piston 201, a dosing chamber gear 311 is arranged. The dosing chamber gear may be realized as combination of a helical reduction gear and a linear displaceable threaded spindle that acts on the dosing piston 201 via releasable engagement for displacing the dosing piston 201 in proximal or distal direction, respectively.

The valve drive 320, 321 includes a valve actuator 321 that may be realized in the same way as the dosing chamber actuator 310, and is in the following considered as rotary valve driver motor. An output shaft of the valve driver motor 320 is, in an operational state, coupled to the filling valve 204a, 205b and the draining valve 205a, 205b via a valve driver gear 321 which may be realized as combination of a helical reduction gear and coupler for releasable rotational engagement with the filling valve 204a, 204b, and the draining valve 205a, 205b.

The control unit 300 is typically realized as controller-based circuitry. The control unit 300 includes a dosing chamber volume controller 302 that is operatively coupled to and controls operation of the dosing chamber actuator 310. Similarly, the control unit 300 includes a valve controller 304 that is operatively coupled to and controls operation of the valve actuator 321.

The control unit 300 further includes a pressure sensor interface 303 that is, in an operational state, coupled to the pressure sensor 203. The kind of coupling depends on the design and operational principle of the pressure sensor 203. In case of the pressure sensor 203 being, e.g. a piezo-resistive or capacitive sensor, the coupling is typical electric. In case of the pressure sensor 203 being an optical sensor, the coupling may also be optical. The pressure sensor interface 303 includes all circuitry that is required for coupling the pressure sensor 203 to a central control unit 301 as discussed below. The pressure sensor interface may especially include components such as sensor power supply, amplifiers, filters, analogue-to-digital converters and/or further signal conditioning circuitry.

The control unit 300 further includes a central controller 301 that controls the overall operation of the ambulatory infusion device 30 and is operatively coupled to the dosing chamber volume controller 302, the valve controller 304, and the pressure sensor interface. The central controller controls the overall operation of the ambulatory infusion device 300. The central controller 301 is typically realized by a single or multitude of components such as micro controllers micro processors, ASICS, and peripheral components.

The different functional units of the control 300 as shown in FIG. 2 does not imply any specific hardware structure. Some or all functional units that are shown distinct from each other in FIG. 2 may be realized, fully or partly, by common hardware components; similarly, a functional unit may be distributed over a number of hardware components.

A housing (not shown) may be present that houses the shown and further components of the ambulatory infusion device 30 and may removable receive the drug reservoir 10 and the dosing unit 20 in corresponding housing compartments, thus forming an operational ambulatory infusion system. The drug reservoir 10 and the dosing unit 20 may also be provided as combined module. Furthermore, either or both of the drug reservoir 10 and the dosing unit 20 may be attached to a housing of the ambulatory infusion device 30 rather than being received by a housing compartment.

The design of the dosing unit 20, the dosing chamber drive 310, 311, and the valve drive 321, 322, may follow the disclosure of the European patent application EP13195599.9. For a number of aspects, however, modifications or alternative solutions are available. In the EP13195599.9, the filling valve and the draining valve are operated by rotating a shut-off body via a valve drive that is separate from the dosing chamber drive. Alternatively, valve switching may be obtained by rotating or shifting the dosing cylinder 200 relative to a stationary part as disclosed, e.g. in the before mentioned EP1970677A1 (see, e.g. FIG. 1) or EP2163273A1. Furthermore, a single common actuator, such as a single rotary motor, may be used for both valve switching and piston displacement.

In the before-mentioned designs, the filling valve 204a, 204b, and the draining valve 205a, 205b, are further realized by a common valve unit that ensures by virtue of its design that only one of the filling valve and the draining valve may be open at the same time. Alternatively, the filling valve 204a, 204b and the draining valve 205a, 205b may be realized as separate switching valves or control valves that may be controlled by a common or separate actuator(s). For such embodiments, simultaneous opening of both valves may be prevented by the valve design, e.g. via mechanical interlocking, or by a corresponding control logic of the control unit 300.

Furthermore, the dosing unit 20 may include a pump different from a piston pump with the dosing cylinder 200 and the dosing piston 2011.

Figure 3:
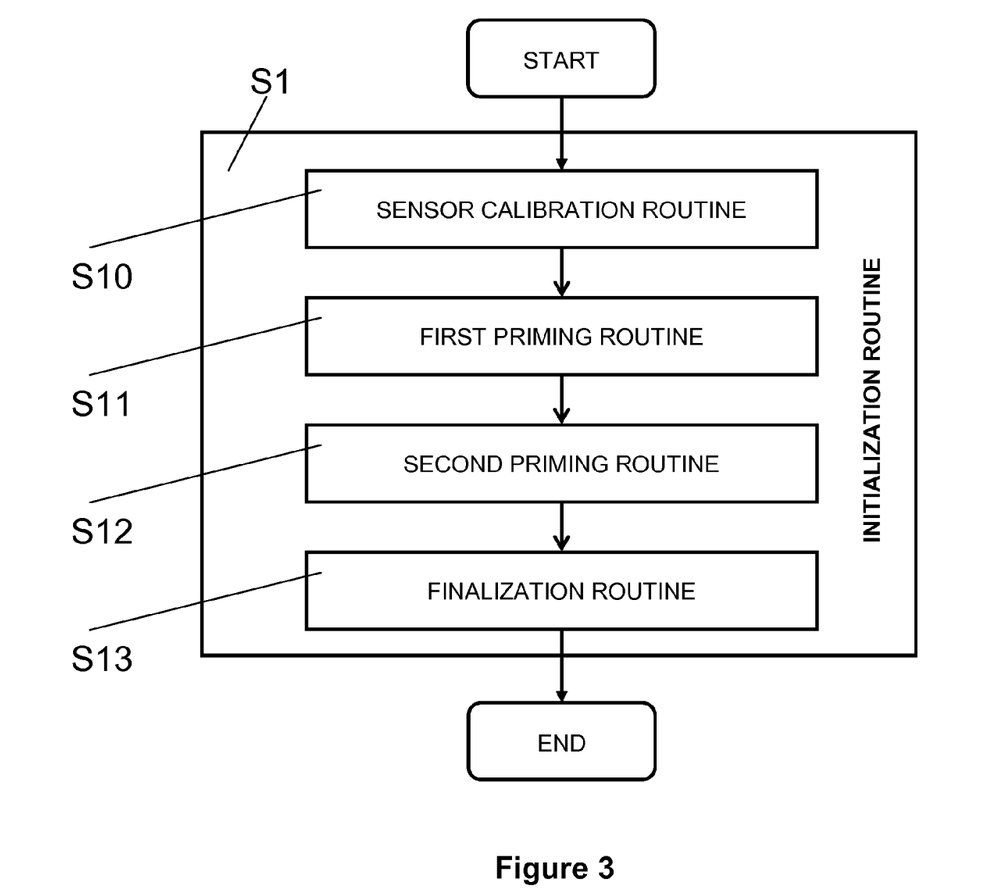
FIG. 3: shows the operational flow of a sequence, the sequence including a pressure calibration routine, a first priming routine, a second priming routine, and a finalization routine.

FIG. 3 shows the operational flow of a method for initializing a dosing unit in accordance with the present disclosure in a schematic view. The steps of the method, in combination, are referred to as step S1. Step S1 includes a sensor calibration routine with steps S10, a first priming routine with steps S11, a second priming routine with steps S12, and an additional finalization routine with steps S13 in sequential order.

Figure 4:
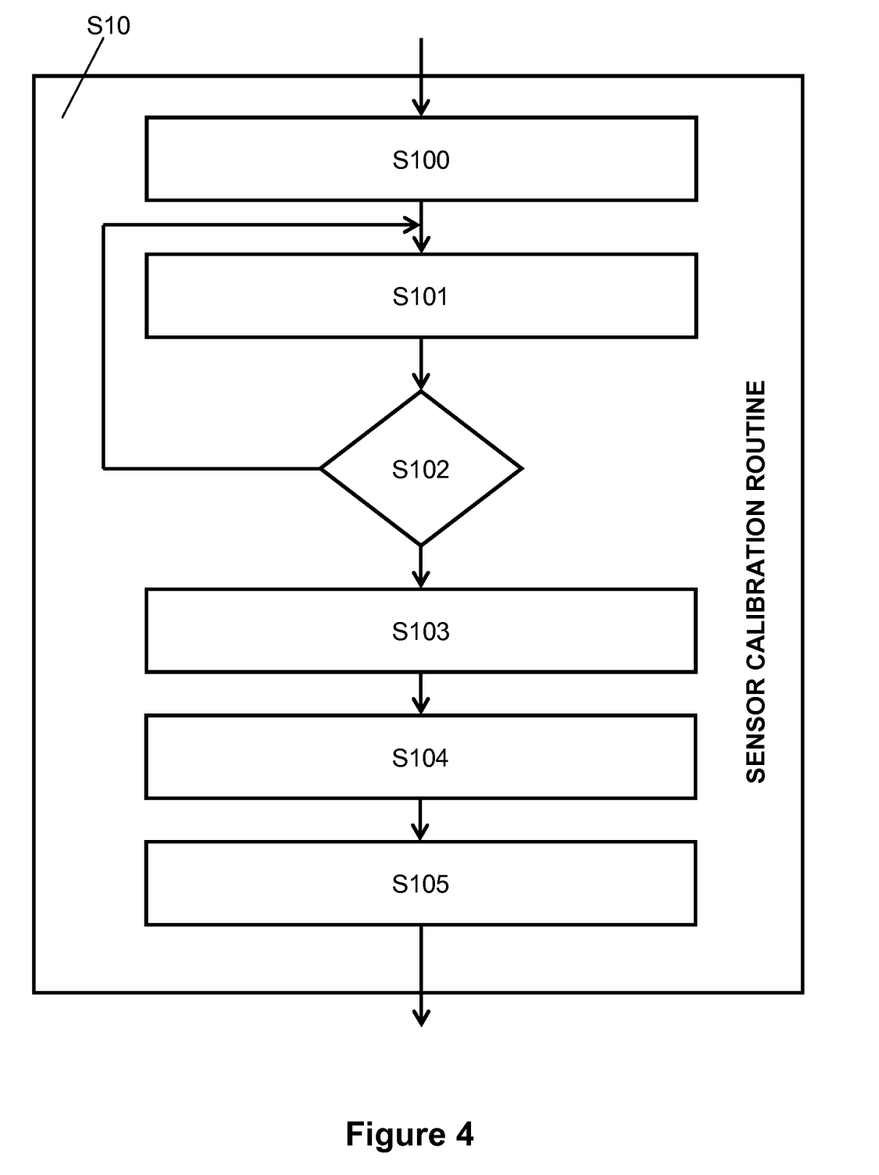
FIG. 4: shows the operational flow of a sensor calibration routine.

FIG. 4 shows the operational flow of a sensor calibration routine S10, with the sensor calibration routine including steps S100, S101, S102, S102, S103, S104, S105 in sequential order. In the initial step S100, both the filling valve and the draining valve are closed.

The step S100 includes determining the state of the filling valve 204 and the draining valve 205 and closing the filling valve 204 or the draining valve if not closed. It is assumed that the dosing cylinder 201 is filled with (sterile) air or an other inert gas. Alternatively, the step 100 may include, prior to closing both the filling valve and the draining valve, increasing the volume of the metering chamber 202, thus filling the dosing cylinder 200 with air in a configuration where the draining valve 205 is open.

In the following step S101, the dosing chamber volume is decreased to a preset compression factor $c_1$ by displacing the piston 201 into the proximal direction, thereby decreasing the dosing chamber volume. A typical suited value for the compression factor $c_1$ is, e.g. $c_1=2$, corresponding to a reduction of the dosing chamber volume by half. For a piston-type dosing unit where the minimum chamber volume is zero, this corresponds to a piston displacement by half of its total displacement range between the maximum and minimum dosing chamber volume.

In the following step S102, the output value of the pressure sensor 203 at the compression factor $c_1$ is read.

In the subsequent step S103, a pressure sensor calibration is computed and stored. In case of a substantially linear relationship between the pressure p and the corresponding output value p* of the pressure sensor 203, it may be sufficient in step S103 to determine the slope m of a linear calibration function $p=m \cdot p^*$. In a variant, the sensor calibration routine S10 includes, prior to closing both the filling valve and the draining valve in step S100, reading and storing an offset output value $p_0^*$ of the pressure sensor 203 in a state where the draining valve 205b is open and the dosing chamber 202 is accordingly vented, via the draining valve 205b, to the environment. In such embodiment, a sensor calibration $p=m \cdot p^* + p_0$ may be computed in step S103, where $p_0$ is an offset pressure that is measured by the pressure sensor 203 at the environmental reference pressure.

In a further variant, a sequence comprising the step S101 of reducing the dosing chamber volume and the following step S102 of reading the output value p* of the pressure sensor is carried out repeatedly. For this type of embodiment, the dosing chamber volume is reduced in equal or non-equal compression steps by displacing the piston 201 in a number of displacement steps, and the output value of the p* is read and stored in each step. For this type of embodiment, the step S103 includes determining a non-linear relationship p=f(p*) using generally known best-fit or regression algorithms.

The before described steps S101, S102, S103 are based on a calibration method where the gas inside the dosing chamber is compressed to one or more pre-set compression factor(s) and the sensor output value(s) is/are read for this/those compression factor(s). Alternatively, however, the step S101 may include reducing the dosing chamber volume and reading the pressure sensor output continuously until the pressure sensor output value assumes a pre-set output value $p_1^*$. For this type of embodiment, the subsequent step S102 includes determining the corresponding pressure $p_1$ from the piston displacement in step S101.

In the subsequent step S104, the draining valve 205 is opened with the filling valve 204 staying closed. Thereby, the compressed gas is partly expelled out of the dosing chamber via the draining valve until the pressure inside the dosing chamber equals the environmental pressure. In the further subsequent step S105, the dosing chamber volume is further decreased to the minimal dosing chamber volume by displacing the piston in the proximal direction. Thereby, the dosing cylinder 101 is emptied and the remaining gas is expelled out of the dosing chamber 202.

Figure 5:
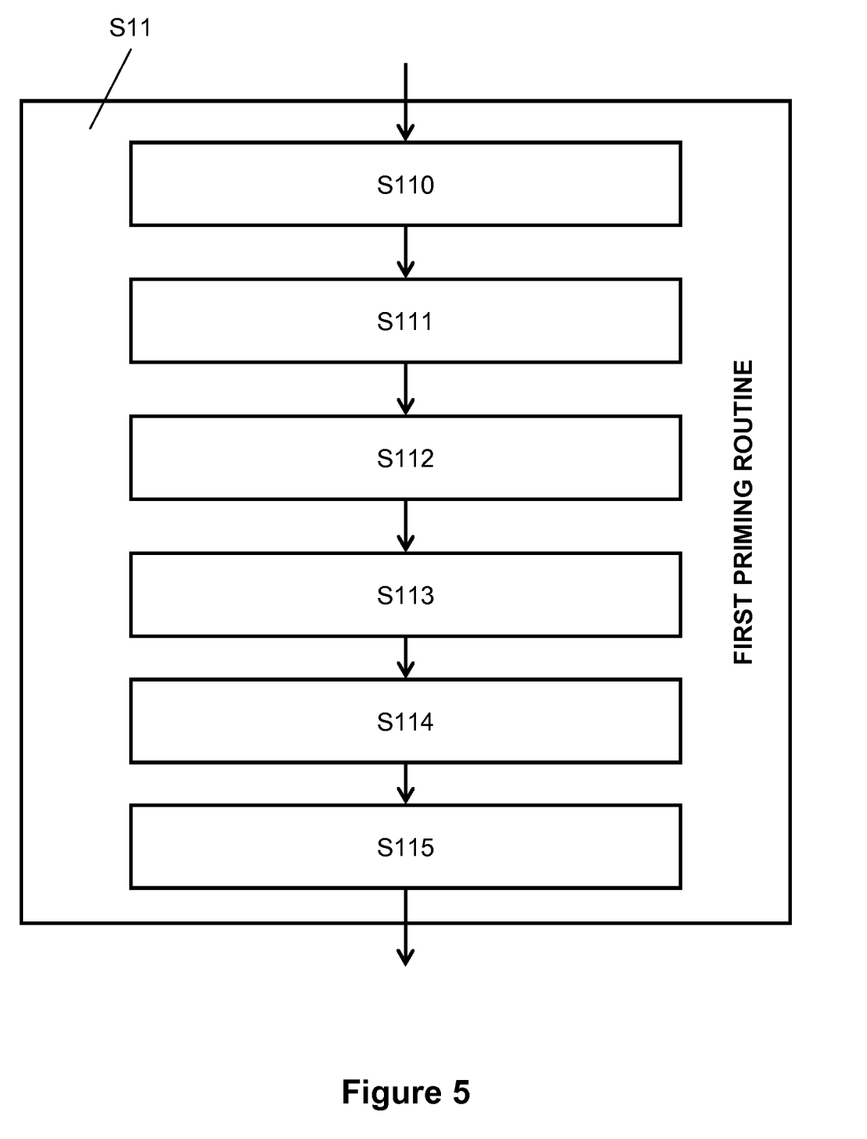
FIG. 5: shows the operational flow of a first priming routine.

FIG. 5 shows the operational flow of a first priming routine S11, with the first priming routine S11 including steps S110, S111, S112, S113, S114, S115. It is assumed that the dosing chamber volume is the minimal dosing chamber volume at the beginning of the first priming routine S11.

In the step S110, the filling valve 204 is opened and the draining valve 205 is closed. The step S110 may include, prior to a valve actuation, determining the state of the filling valve 204 and the draining valve 205, respectively. The step S110 may further include carrying out a valve actuation only if the filling valve 204 is not opened and/or the draining valve 205 is not closed.

In the subsequent step S111, the reservoir fluid pressure $p_2$ is measured by reading and evaluating the output signal provided by the pressure sensor 203.

In the subsequent step S112, a first priming volume $v_1$ is computed based on the previously measured reservoir fluid pressure $p_2$ according to the above-discussed formula $$v_1 = V_0 \cdot \frac{P_{ref}}{P_{ref} + p_2} + V_S.$$

In the subsequent step S113, the dosing chamber volume is increased by the first priming volume $v_1$, which is achieved by displacing the piston 201 into the distal direction. At the end of the piston displacement in the step S113, the dosing chamber corresponds a mixture of air and gas in dependence of the reservoir fluid pressure $p_2$. The reservoir coupling conduit, however, is in any case filled with liquid drug.

In the subsequent step S114, the filling valve 204 is closed and the draining valve 205 is opened instead. In the further subsequent step S115, the dosing chamber volume is decreased to the minimal dosing chamber volume by displacing the piston into the proximal direction. Thereby, the mixture of air and liquid drug is expelled via the draining valve and the dosing unit is empty at the end of the step S115.

Figure 6:
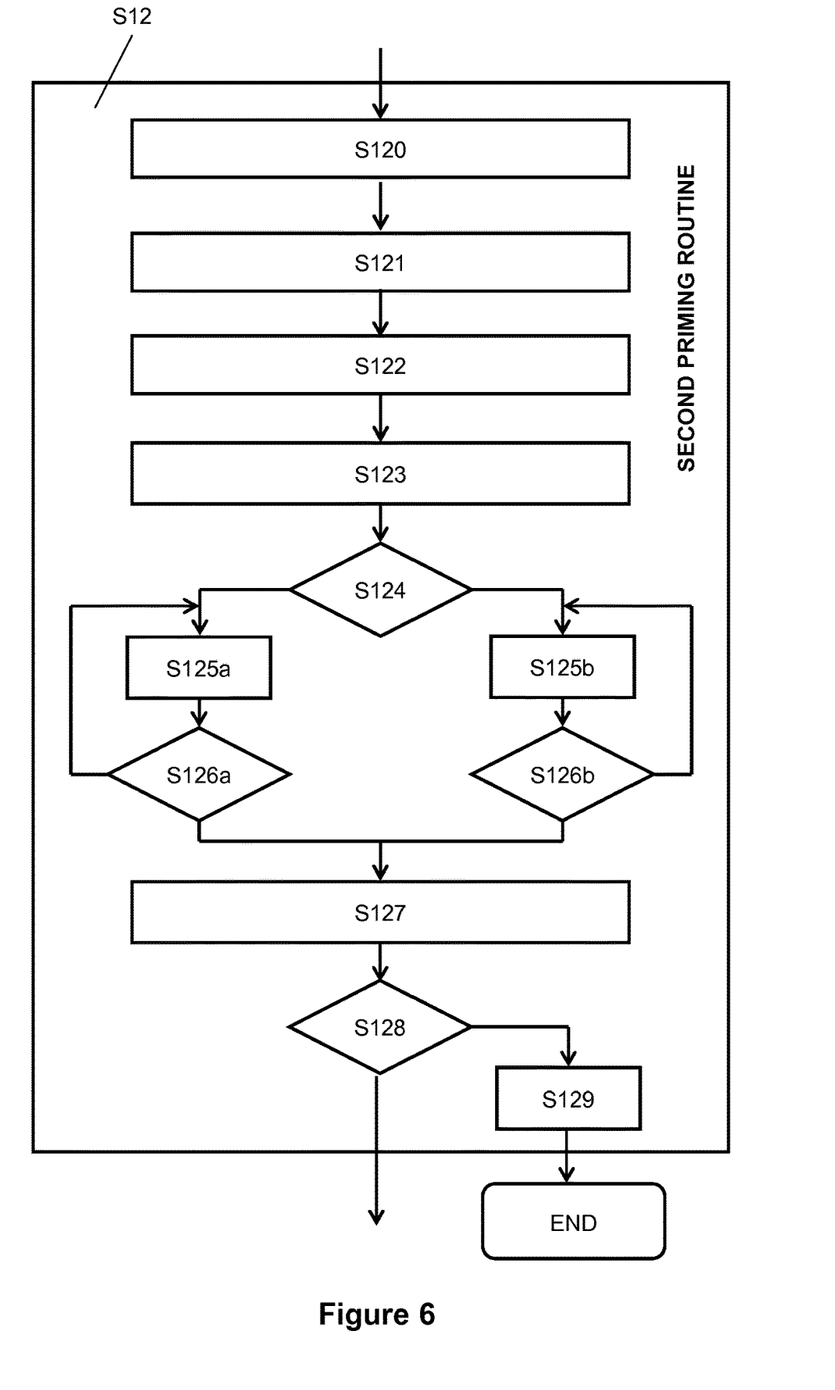
FIG. 6: shows the operational flow of a second priming routine.

FIG. 6 shows the operational flow of a second priming routine S12, with the second priming routine S12 including steps S120, S121, S122, S123, S124, S125a, S125b, S126a, S126b, S127, S128, and S129. It is assumed that the dosing chamber volume is the minimal dosing chamber volume at the beginning of the first priming routine S12.

In step S120, the filling valve 204 is opened and the draining valve 205 is closed. The step S120 may include, prior to a valve actuation, determining the state of the filling valve 204 and the draining valve 205, respectively. The step S110 may further include carrying out a valve actuation only if the filling valve 204 is not opened and/or the draining valve 205 is not closed.

In the subsequent step S121, the dosing chamber volume is increased by a second priming volume $v_2$, which is achieved by displacing the piston 102 into the distal direction. Increasing the dosing chamber volume by the second priming volume $v_2$ results in sucking a second priming amount of liquid drug reservoir 10 into the dosing chamber. The second priming amount of liquid drug may be identical to the second priming volume $v_2$ if no air/gas is suck from the liquid drug reservoir; otherwise, the second priming amount of liquid drug is smaller than the second priming volume $v_2$ and a the dosing chamber is filled with a mixture of liquid drug and air/gas at the end of step S121.

In the subsequent step S122, the filling valve 204 is closed with the draining valve 205 staying closed, resulting in the dosing chamber being fluidic isolated.

In the subsequent step S123, the chamber pressure $p_C$ is measured by reading and evaluating the output value of the pressure sensor 203. In the subsequent step S124, the operational flow branches in dependence on whether the dosing chamber pressure $p_C$ is positive or negative, that is, whether there is an over- or under pressure relative to the reference pressure $P_{ref}$. The measured chamber pressure $p_C$ is stored as initial chamber pressure value $p_{C,0}$.

If the dosing chamber pressure $p_C$ is positive, the dosing chamber volume is increased in the step S125a by displacing the piston 201 by an incremental step in the distal direction, thereby decreasing the positive chamber pressure $p_C$. In the subsequent step S126a, it is determined, by reading and evaluating the output value of the pressure sensor 203, if the dosing chamber pressure $p_C$ equals the reference pressure $P_{ref}$. If this is the case, the operational flow proceeds with step the S127. Otherwise, the operational flow proceeds with repeating the step S125a.

If the dosing chamber pressure $p_C$ is negative, the dosing chamber volume is decreased in the step S125b by displacing the piston 201 by an incremental step in the proximal direction, thereby decreasing the absolute value of the negative chamber pressure $p_C$. In the subsequent step S126b, it is determined, by reading and evaluating the output value of the pressure sensor 203, if the dosing chamber pressure equals the reference pressure $p_{ref}$. If this is the case, the operational flow proceeds with step the S127. Otherwise, the operational flow proceeds with repeating the step S125b.

When repeatedly carrying out the sequence of steps S125a, S126a, or S125a, S126b, respectively, the number of displacement steps m of the piston 201 that is required for equalizing the dosing chamber pressure $p_C$ with the reference pressure $P_{ref}$ is counted.

After equalling the dosing chamber pressure $p_C$ with the reference pressure $P_{ref}$ in steps S125a and S126a, or S125b and S126b, respectively, the operational flow proceeds with the step S127. In the step S127, an amount of air $V_{air}$ inside the dosing chamber is computed based on the above-discussed formula:

$$V_{air} = (m - m_{compliance}) \cdot V_{step} \cdot \left(1 + \frac{P_{ref}}{p_{c,0}}\right).$$

In the subsequent step S128, the air volume $V_{air}$ as computed in the step S127, is compared with a pre-set threshold air volume $V_{air,threshold}$. If the air volume $V_{air}$ exceeds the threshold air volume $V_{air,threshold}$, an alert is provided in the step S129.

Figure 7:
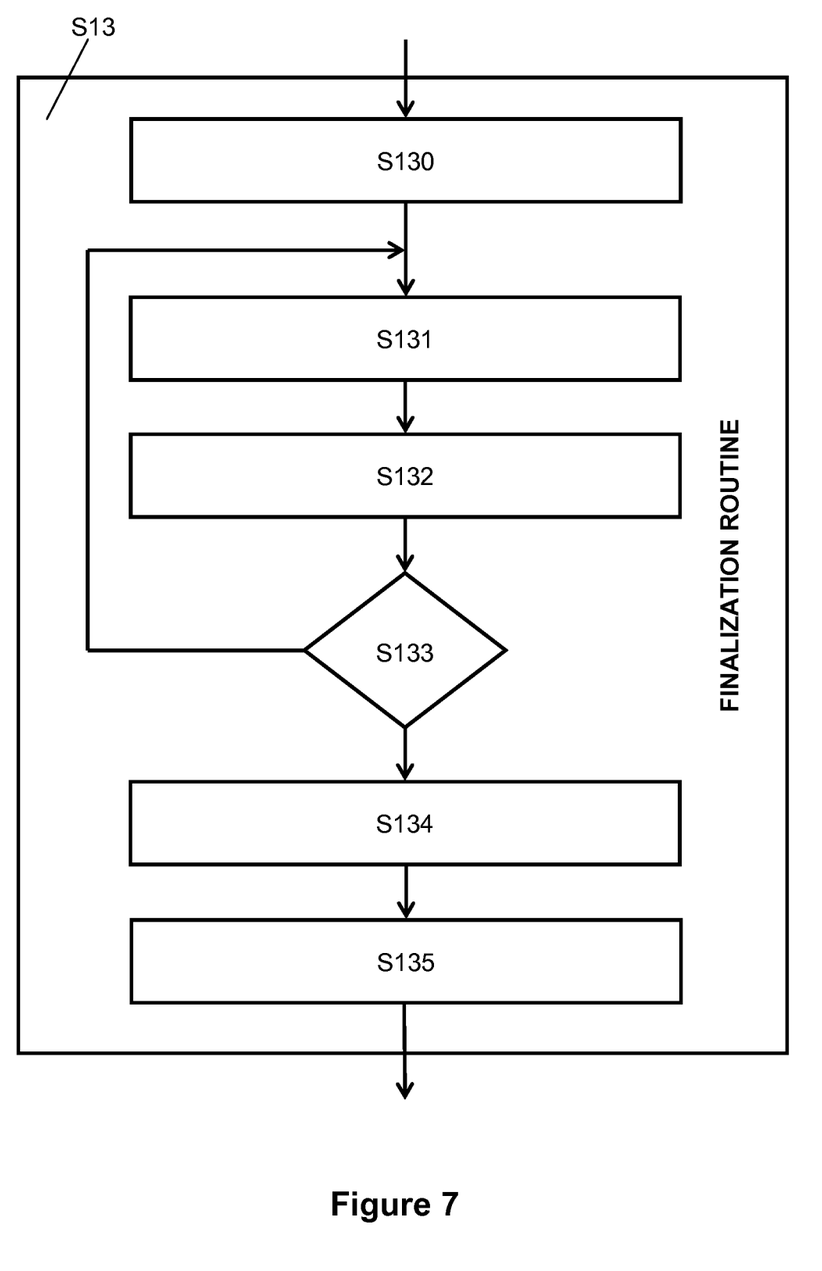
FIG. 7: shows the operational flow of a finalization routine.

FIG. 7 shows the operational flow of a finalization routine S13, the finalization routine S13 following the second priming routine S12 and including the steps S130, S131, S132, S133, S134.

In the step S130, the dosing chamber volume is increased by displacing the piston 201 by $m_S$ steps in the distal direction, thereby creating a negative pressure inside the dosing chamber. The number of steps $m_S$ is determined such that resulting piston displacement is somewhat larger than the mechanical backlash resulting from reversing the displacement direction of the piston 201.

In the subsequent step S131, the dosing chamber volume is decreased by displacing the piston 201 by an incremental step in the proximal direction. In the subsequent step S132, the chamber pressure $p_C$ is measured by reading and evaluating the output value of the pressure sensor 203.

In the subsequent step S133, it is determined if the dosing chamber pressure $p_C$ equals the reference pressure $p_{ref}$. If this is the case, the operational flow proceeds with step S134. Otherwise, the operational flow proceeds with step S131.

In the subsequent step S134, the draining valve 205 is opened with the filling valve 204 staying closed. In the subsequent step S135, the dosing chamber volume is decreased to the minimal chamber volume by displacing the piston 102 in the proximal direction. Thereby, the liquid drug is expelled, via the draining valve 205 out of the dosing chamber and into the infusion line 50, thus priming the infusion line 500.

The second priming routine and the finalization routine may not only be carried out in the context of initialization and priming, but may be carried out for (refilling) the dosing chamber during subsequent regular infusion operation. This is approach is particularly favourable since it involves a air volume computation and favourably providing an alarm in case of an excessive air volume every time the dosing chamber of the dosing unit is (re-)filled. Therefore, these routines also disclose a method for filling or refilling a dosing chamber of a dosing unit of the described type.

The invention claimed is:

1. Method for initializing a dosing unit of an ambulatory infusion system, the method including carrying out a first priming routine, the first priming routine including:
   providing the dosing unit with a dosing chamber of the dosing unit having a minimal dosing chamber volume, a draining valve of the dosing unit being closed and a filling valve of the dosing unit being open;
   measuring an initial reservoir fluid pressure $p_2$ and computing, based on the initial reservoir fluid pressure $p_2$, a first priming volume $v_1$, with a liquid drug reservoir being fluidically coupled with the dosing chamber via a reservoir coupling conduit and the opened filling valve;
   increasing the dosing chamber volume by the first priming volume $v_1$, with the first priming volume $v_1$ being computed such that the reservoir coupling conduit is filled with liquid drug substantially completely at the end of the dosing chamber volume increasing;
   closing the filling valve and opening the draining valve;
   emptying the dosing unit by decreasing the dosing chamber volume to the minimal dosing chamber volume.

2. Method according to claim 1, wherein the method further includes, prior to carrying out the first priming routine, carrying out a sensor calibration routine, the sensor calibration routine including:
   providing the dosing unit in an initial state with the dosing chamber being gas-filled and both of the filling valve and the draining valve being closed, resulting in the dosing chamber being fluidic isolated;
   decreasing the dosing chamber volume, thereby compressing the gas inside the dosing unit to a compression factor $c_1$;
   reading, at the compression factor $c_1$, an output value $p_1^*$ of a pressure sensor in fluidic coupling with the dosing chamber and computing, based on the output value $p_1^*$ and the compression factor c, a pressure sensor calibration, and storing the computed calibration;
   opening the draining valve with the filling valve staying closed; and
   emptying the dosing unit by further decreasing the dosing chamber volume to the minimal dosing chamber volume.

3. Method according to claim 1, wherein the method further includes, following carrying out the first priming routine, carrying out a second priming routine, the second priming routine including:
   closing the draining valve and opening the filling valve;
   increasing the dosing chamber volume by a second priming volume;
   closing the filling valve with the draining valve staying closed, resulting in the dosing chamber being fluidic isolated;
   varying the dosing chamber volume and monitoring, during the variation, a dosing chamber pressure $p_C$, and stopping the variation upon the dosing chamber pressure $p_C$ equalling a reference pressure; and
   computing, based on an amount of variation of the dosing chamber volume, an air volume $V_{air}$ of air inside the dosing chamber.

4. Method according to claim 3, wherein the second priming routine includes: the comparing the air volume $V_{air}$ with a pre-set threshold air volume $V_{air,threshold}$ and providing an alert if the air volume $V_{air}$ exceeds the pre-set threshold air volume $V_{air,threshold}$.

5. Method according to claim 3, wherein the second priming routine includes: taking into account a mechanical compliance of limiting walls of the dosing chamber for computing the air volume $V_{air}$.

6. Method according to claim 1, wherein the minimal dosing chamber volume is negligible or zero.

7. Method according to claim 1, wherein the first priming routine includes: computing the first priming volume $v_1$ as $$v_1 = V_0 \cdot \frac{p_{ref}}{p_{ref} + p_2} + V_S,$$

with $V_0$ being the fluidic volume of the reservoir coupling conduit, $P_{ref}$ being a reference pressure, and $V_s$ being a safety margin volume.

8. Method according to claim 1, wherein increasing of the dosing chamber volume is achieved by displacing a piston of the dosing unit into a distal direction, and wherein decreasing of the dosing chamber volume is achieved by displacing the piston into an opposite proximal direction, with the piston being received in a dosing cylinder of the dosing unit and the dosing cylinder extending along a piston displacement axis, thus forming a movable limiting wall of the dosing chamber.

9. Method according to claim 1, wherein opening and closing of the filling valve and the draining valve between an open and a closed state includes rotating a common shutoff body of the dosing unit.

10. Control unit, the control unit being designed for controlling operation of a dosing unit of an ambulatory infusion system, the control unit including a dosing chamber volume controller, a valve controller and a pressure sensor interface, the control unit being further designed for controlling execution of an initialization routine, the initialization routine including a first priming routine, the first priming routine causes the control unit to:
provide a dosing chamber of the dosing unit with a minimal dosing chamber volume, a draining valve of the dosing unit and open a filling valve of the dosing unit;
measure an initial reservoir fluid pressure $p_2$ and compute, based on the initial reservoir fluid pressure $p_2$, a first priming volume $v_1$, with the liquid drug reservoir being fluidically coupled with the dosing chamber via a reservoir coupling conduit and the opened filling valve;
increase the dosing chamber volume by the first priming volume $v_1$, with the first priming volume $v_1$ being computed such that the reservoir coupling conduit is filled with liquid drug substantially completely at the end of the increase in the dosing chamber volume;
close the filling valve and open the draining valve; and
empty the dosing unit by a decrease in the dosing chamber volume to the minimal dosing chamber volume.

11. Control unit according to claim 10, the control unit being further designed for controlling, prior to controlling execution of the first priming routine, execution of a sensor calibration routine, the sensor calibration routine causes the control unit to:
close the filling valve and the draining valve, which results in the dosing chamber being fluidic isolated;
decrease the dosing chamber volume, thereby compressing gas inside the dosing unit to a compression factor $c_1$;
read, at the compression factor $c_1$, an output value $p_1^*$ of a pressure sensor in fluidic coupling with the dosing chamber and compute, based on the output value $p_1^*$ and the compression factor c, a pressure sensor calibration, and store the computed calibration;
open the draining valve with the filling valve staying closed; and
empty the dosing unit by a further decrease in the dosing chamber volume to the minimal dosing chamber volume.

12. Control unit according to claim 10, the control unit being further designed for controlling, following execution of the first priming routine, execution of a second priming, the second priming causes the control unit to:
close the draining valve and open the filling valve;
increase the dosing chamber volume by a second priming volume $v_2$;
close the filling valve with the draining valve staying closed, which results in the dosing chamber to be fluidic isolated;
vary the dosing chamber volume and monitor, during the variation, a chamber pressure $p_C$ inside the dosing chamber, and stop the variation upon the chamber pressure $p_C$ equalling a reference pressure $p_{ref}$; and
compute, based on an amount of variation of the dosing chamber volume, an air volume $v_{air}$ of air inside the dosing chamber.

13. Control unit according to claim 10, wherein the dosing chamber volume controller is designed for controlling a dosing chamber actuator to alternatively increase or decrease the dosing chamber volume continuously or in incremental steps.

14. Control unit according to claim 10, wherein the valve controller is designed for controlling a rotary valve motor as a valve actuator and the dosing chamber volume controller is designed for controlling a rotary dosing chamber motor as a dosing chamber actuator.

15. Ambulatory infusion device, including:
a control unit according to claim 10;
a valve actuator, the valve actuator being operatively coupled to the valve controller and being designed for engaging a valve actuator coupler of a dosing unit;
a dosing chamber actuator, the dosing chamber actuator being operatively coupled to the dosing chamber actuator controller and being designed for engaging a movable limiting wall of the dosing chamber;
a casing, the casing enclosing the control unit, the valve actuator and the dosing chamber actuator; and
a dosing unit interface, the dosing unit interface being designed for releasably coupling the ambulatory infusion device with the dosing unit such that the valve actuator releasably engages a valve actuator coupler of a dosing unit.

* * * * *

UNITED STATES PATENT AND TRADEMARK OFFICE
CERTIFICATE OF CORRECTION

PATENT NO. : 10,159,784 B2  
APPLICATION NO. : 15/126628  
DATED : December 25, 2018  
INVENTOR(S) : David Teutsch et al.

Page 1 of 1

It is certified that error appears in the above-identified patent and that said Letters Patent is hereby corrected as shown below:

In the Claims

Column 16, Line 14, Claim 2:
"dosing chamber being fluidic isolated"
Should read:
--dosing chamber being fluidically isolated--;

Column 16, Line 35, Claim 3:
"closed, resulting in the dosing chamber being fluidic"
Should read:
--closed, resulting in the dosing chamber being fluidically--;

Column 17, Line 43, Claim 11:
"results in the dosing chamber being fluidic isolated;"
Should read:
--results in the dosing chamber being fluidically isolated;--;

Column 18, Line 16, Claim 12:
"fluidic isolated;"
Should read:
--fluidically isolated;--.

Signed and Sealed this
Ninth Day of July, 2019

Andrei Iancu
*Director of the United States Patent and Trademark Office*